United States Patent [19]
Zander

[11] Patent Number: 6,160,097
[45] Date of Patent: *Dec. 12, 2000

[54] PROCESS FOR REACTIVATING PURIFIED MEMBRANE PROTEINS BY FREEZING THEM

[75] Inventor: Norbert F. Zander, Marburg, Germany

[73] Assignee: Dade Behring Marburg GmbH, Marburg, Germany

[ * ] Notice: This patent is subject to a terminal disclaimer.

[21] Appl. No.: 09/481,699

[22] Filed: Jan. 12, 2000

Related U.S. Application Data

[62] Division of application No. 08/397,952, Mar. 3, 1995.

[30] Foreign Application Priority Data

Mar. 5, 1994 [DE] Germany ............................. 44 07 386

[51] Int. Cl.[7] .................................................. C07K 14/745
[52] U.S. Cl. .......................... 530/381; 530/380; 530/413; 530/427; 514/21
[58] Field of Search ..................................... 530/381, 380, 530/413, 427, 402; 514/21; 424/450

[56] References Cited

U.S. PATENT DOCUMENTS

| | | | |
|---|---|---|---|
| 5,426,031 | 6/1995 | Hawkins et al. ......................... | 530/381 |
| 6,031,081 | 2/2000 | Zander ..................................... | 530/381 |

OTHER PUBLICATIONS

Brotherus et al., "Soluble and Enzymatically Stable (Sodium, Potassium)—ATPase from Mammalian Kidney Consisting Predominatly of Protomer αβ–units: Preparation, Assay and Reconstruction of Active Sodium, Potassium Transport," Biological Abstracts 76(10):7890, Abstract 71791 (1983).

De Post et al., "Quantitative Assessment of Procoagulant Activity in Isolated Rat Glomeruli," Chemical Abstracts 104(3):342–43, Abstract 18027a (1986).

Sasaki et al., "Molecular Mechanism of Regulation of $Ca^{2+}$ Pump ATPase by Phospholamban in Cardiac Sarcoplasmic Reticulum," Journal of Biological Chemistry 267(3):1674–79 (1992).

Contino et al., "Use of an Oriented Transmembrane Protein to Probe the Assembly of a Supported Phospholipid Bilayer," Chemical Abstracts 121(19):566, Abstract 225786c (1994).

Jones et al., "Solubilization and Reconstruction of Membrane Proteins," Biosis #87:494121 (1987) whole document (pp.139–176).

Rehemtulla et al., "High Level Expression of Recombinant Human Tissue Factor in Chinese Hamster Ovary Cells as a Human Thromboplastin," Thrombosis and Haemostasis, v.65(5), pp. 521–527 (1991).

Bach et al., "Factor VII Binding to Tissue Factor in Reconstituted Phospholipid Vesicles: Induction of Cooperativity by Phosphatidylserine," Biochemistry, v. 25, pp. 4007–4020 (1986).

Guha, et al., "Affinity purification of human tissue factor: Interaction of factor VII and tissue factor in detergent micelles," Proc. Natl. Acad. Sci., USA, v. 83, pp. 299–302 (Jan. 1986).

*Primary Examiner*—Christopher S. F. Low
*Assistant Examiner*—Patricia Robinson
*Attorney, Agent, or Firm*—Finnegan, Henderson, Farabow, Garrett and Dunner, L.L.P.

[57] ABSTRACT

A process is described for reactivating purified membrane proteins in which a mixture composed of membrane protein, a phospholipid and a detergent is frozen and subsequently thawed.

12 Claims, 1 Drawing Sheet

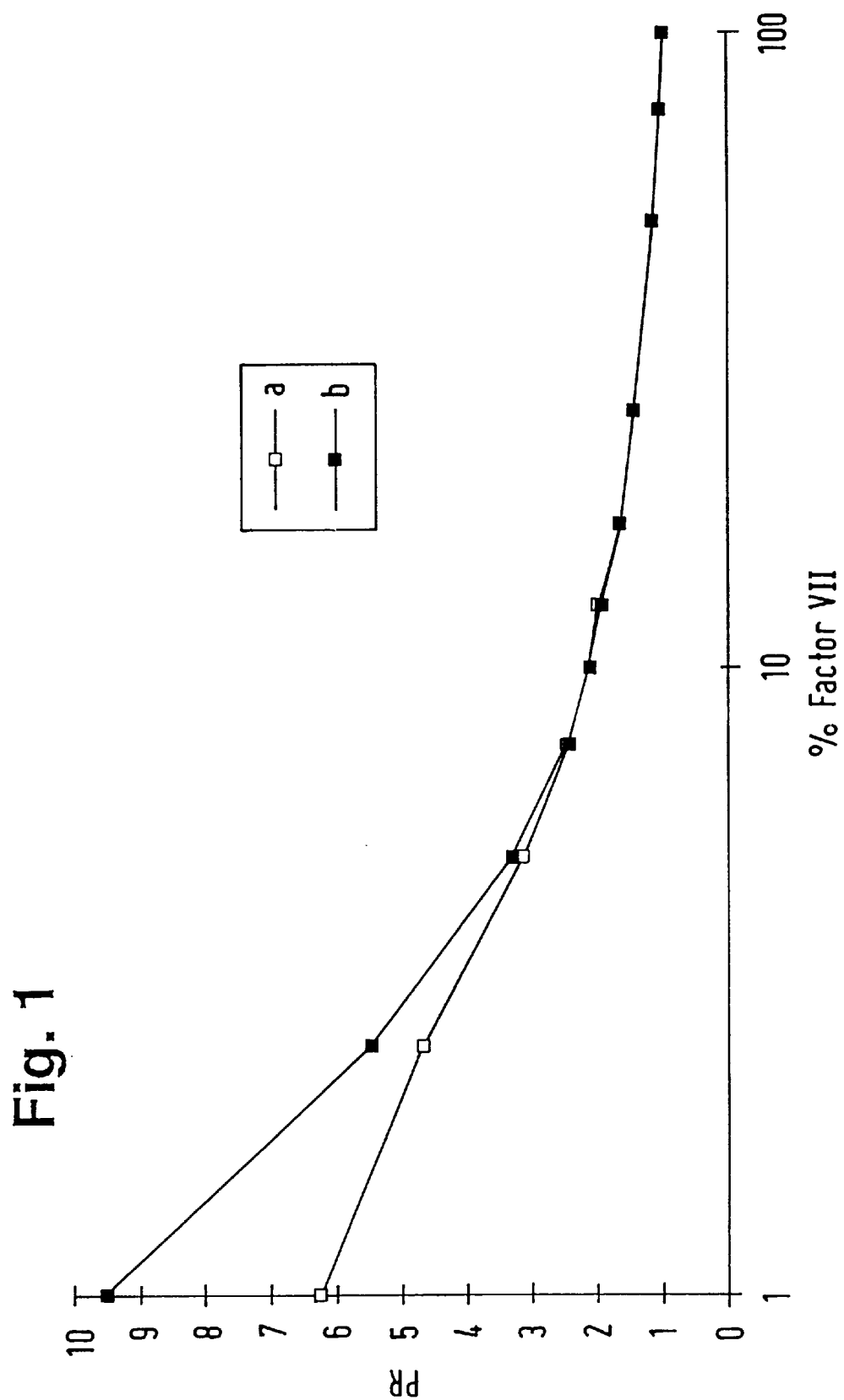

PROCESS FOR REACTIVATING PURIFIED MEMBRANE PROTEINS BY FREEZING THEM

This is a divisional of application Ser. No. 08/397,952 filed Mar. 3, 1995.

The invention relates to a process for reactivating purified membrane proteins so that they become active proteins.

Membrane proteins, e.g. receptors, are composed of one or more transmembrane domains and also intracellular and extracellular domains. The activity of a protein of this type is frequently measured following integration of the purified protein into an artificial membrane.

Tissue factor (tissue thromboplastin) can be taken as an example. This receptor for factor VII is composed of apoprotein and lipids. The apoprotein is a glycosylated polypeptide of 263 amino acids. Near to the carboxyl-terminal end, it possesses a hydrophobic sequence of 23 amino acids by which it is anchored in the membrane. The intracellular moiety is composed of 21 amino acids. In vivo, tissue factor is present as an integral membrane protein in cells which are not in direct contact with blood. As a cell surface receptor, its physiological function comprises, on contact with blood or plasma, binding the plasma coagulation factor VII and activating it. This complex possesses serine protease activity and is, for its part, able to activate factors IX and X and trigger coagulation.

Two methods for isolating tissue factor can be distinguished. In the first, active tissue factor is partially purified by disrupting a suitable tissue and isolating the corresponding membrane fraction. This material is used, in the first instance, in the preparation of reagents which are employed diagnostically for testing plasma blood coagulation. Since the membrane protein is isolated in its entirety (i.e. including bound lipid molecules), reactivation of the apoprotein is not required.

The second process involves obtaining the isolated apoprotein. Since the latter scarcely has any activity left, it has to be reactivated. For this, it must be reintegrated into a lipid membrane. This procedure is essential for protein which is obtained recombinantly, since the microbiological organisms which are employed for producing it are not, as a rule, able to supply a membrane protein which is sufficiently active. In principle, these considerations also apply to proteins which are prepared in vitro by partial or total synthesis.

A number of methods are known for reincorporating purified membrane proteins into a lipid membrane. For this, phospholipids are customarily brought into aqueous solution using a detergent, e.g. Triton X 100. This solution is then mixed with the membrane protein. After that, the detergent is removed, e.g. by dialysis. During mixing the apoprotein with the phospholipid solution, and removing the detergent, the protein is incorporated into the membrane vesicles which form. Deoxycholate is the preferred detergent since it can be removed by dialysis. However, other detergents can also be used in principle if they can be removed once again from the mixture.

The underlying object of the present invention was to make available a simplified process by which membrane proteins can be integrated as rapidly as possible into lipid vesicles, and thereby be reactivated, using a minimum number of steps.

It has been found, surprisingly, that this relipidization can be achieved simply by freezing a mixture of phospholipids, detergent and membrane protein. Subsequent removal of the detergent from the reaction mixture is not strictly necessary.

In principle, the novel process can also be applied to mixtures of purified proteins.

It has been found that the relipidization can be achieved by freezing a preferably concentrated, liquid, preferably aqueous, mixture of phospholipid, detergent and membrane protein. The freezing can be effected at temperatures of from 0° C. to −200° C., preferably at about −70° C. The rapidity of the freezing is not critical. The period during which the mixture remains in the frozen state can vary between 1 hour and 1 year; the mixture is preferably frozen for about 16 hours. It is expedient for the entire mixture to be frozen through homogeneously. Thawing is effected at from 0° C. to 100° C., preferably at about 37° C.

A material of vegetable or animal origin, which is known per se to the person skilled in the art, can be used, as a natural mixture of known components, as the phospholipid. Pure phospholipids, or mixtures thereof, which are known to the person skilled in the art can also be employed. In the novel process, use is preferably made of mixtures of vegetable phospholipids. The lipid concentration in the mixture to be frozen is preferably from greater than 0 to 500 mg/ml.

The membrane protein can be of human, vegetable, animal, microbial or recombinant origin. It is also possible to activate inactive mutants of naturally occurring proteins.

Preference is given to a protein of this type which is a human, and where appropriate, recombinant protein.

Preference is given to the use of a dissolved membrane protein at a concentration of from greater than 0 to 50 mg/ml.

Nonionic, anionic or cationic detergents, in pure form or mixed together, can be employed as the detergent. The concentration is between greater than 0% and 50%. The novel process is preferably carried out using the non-ionic detergent Triton X 100 at a concentration of 2%.

Preferably, phospholipid is initially emulsified in water or an aqueous liquid at a concentration of from greater than 0% to 50%. Detergent is dissolved in water or an aqueous liquid in a concentration of from greater than 0% to 50%. Phospholipid, detergent and membrane protein are then mixed in a quantity ratio which is suitable in each case. The mixture is frozen at from 0° C. to −200° C. Once the entire mixture is frozen through, it remains at this temperature for a period of between 1 hour and 1 year, preferably 16 hours. It is then thawed at a temperature of between 0° C. and 100° C., preferably at 37° C. The excess detergent can be moved by dialyzing against buffer or be diluted by the addition of a large quantity of buffer such that it no longer interferes in the subsequent reactions.

Freezing preferably takes place in the presence of water. However it also appears possible to freeze a liquid mixture of the components in the absence of water. When being frozen with lipid and detergent, the membrane protein may also be bound to a solid matrix.

After the relipidization, the membrane protein is in active form, incorporated into a lipid membrane. For further use, it can, where appropriate, be provided with additives and formulated.

If, in the novel process, tissue factor apoprotein, for example, is relipidized, it can be used as a therapeutic agent or as a diagnostic agent. In the second instance, the relipidized tissue factor can, in particular, be processed into a reagent for determining the prothrombin time for the purpose of monitoring plasma blood coagulation.

The advantage of the novel process over the known and described processes for relipidizing membrane proteins is that it is simpler to carry out. In particular, the labor-intensive and costly step of dialysis against detergent-free buffer can be dispensed with.

The invention will be illustrated in more detail using tissue factor apoprotein as an example.

EXAMPLES

Example 1

Use of freezing to relipidize a human tissue thromboplastin apoprotein which has been obtained recombinantly and purified The following were mixed together:

| | |
|---|---|
| 30 ml of 10% | phospholipid suspension in distilled water (Phospholipon 25P, from Nattermann) |
| 5 ml of 1 mg/ml | purified human tissue thromboplastin apoprotein |
| 4 ml of 20% | Triton X 100 |
| 1 ml of | distilled water. |

After having been stirred for one hour, the mixture is frozen at −70° for 16 hours. At the end of this period, the mixture is thawed at 37° C. and diluted with 20 1 of:

| | |
|---|---|
| 50 mM | N- (2-hydroxyethyl)piperazine-N' - (2-ethanesulfonic acid), pH 7.5 |
| 13 mM | calcium chloride. |

The prothrombin time was determined using a Schnitger and Gross coagulometer (0.1 ml of normal human plasma pool +0.2 ml of relipidized tissue factor) and gave a coagulation time of 10.8 s.

Example 2

Dependence of the relipidization on temperature

Reagents were prepared essentially as described in Example 1. The mixture of membrane protein, detergent and lipid was frozen at −20° C. and −60° C. and subsequently diluted with buffer.

To serve as negative controls, mixtures of lipid and protein, and of lipid and detergent, were frozen and thawed in the same manner. The component which was still missing, and buffer, were then added and mixed in. The following coagulation times were obtained with a normal human plasma pool using a Schnitger and Gross coagulometer:

TABLE I

Dependence of the freezing step on temperature

| According to the invention | Temperature | Additions | Coagulation time |
|---|---|---|---|
| Lipid/detergent/protein | −20° C. | Buffer | 9.5 s |
| Lipid/detergent/protein | −60° C. | Buffer | 9.5 s |
| Negative controls | | | |
| Lipid/protein | −60° C. | Detergent/buffer | 21.0 s |
| Lipid/detergent | −60° C. | Protein/buffer | 18.7 s |

Example 3

Quality of the reagents: factor VII sensitivity

A normal human plasma pool was diluted with a factor VII-deficient plasma (Behringwerke AG, Marburg, Germany). Factor VII concentrations were employed which were between 100% and 1% (based on the normal human plasma pool).

The prothrombin times of the samples were then determined using a Schnitger and Gross coagulometer. The times which were measured were related to the prothrombin time of the normal human plasma pool. FIG. 1 shows the relative prothrombin times [prothrombin ratio, $PR=(PT)/(PT_{100\% \; factor \; VII})$] plotted against the concentration of factor VII in the sample. Two tissue factor reagents were used:

a native tissue factor, isolated from human placenta (®Thromborel S, Behringwerke AG)

b reagent based on recombinant tissue factor apoprotein, prepared in accordance with the novel process (according to Example 1).

The normal range of factor VII concentration in a human population (95 percentile) is encompassed by prothrombin ratios of 1.00±0.20. Plasmas which have a ratio lying outside this range are considered to be pathological. The factor VII concentration corresponding to this sensitivity limit is very similar for the two reagents examined here.

In the range below 10% factor vii, the reagent based on the recombinant tissue factor apoprotein is clearly more sensitive.

What is claimed is:

1. A process for reactivating a human membrane protein without dialyzing against a detergent-free buffer, comprising:

(a) freezing a liquid comprising the human membrane protein, a lipid, and a detergent; and (b) subsequently thawing the frozen liquid.

2. The process as claimed in claim 1, wherein the human membrane protein is a recombinant protein.

3. The process as claimed in claim 1, wherein a pure lipid, a mixture of pure lipids, or a natural lipid mixture is used.

4. The process as claimed in claim 1, wherein the detergent is used at a concentration of greater than 0% to 50%.

5. The process as claimed in claim 1, wherein a non-ionic detergent is used.

6. The process as claimed in claim 2, wherein freezing takes place at a temperature of 0° C. to −20° C.

7. The process as claimed in claim 1, wherein the human membrane protein is in solution.

8. The process as claimed in claim 1, wherein the human membrane protein is bound to a solid matrix.

9. The process as claimed in claim 1, wherein the concentration of the human membrane protein is from greater than 0 to 50 mg/ml.

10. The process as claimed in claim 1 wherein the lipid concentration is greater than 0 mg/ml to 500 mg/ml.

11. The process as claimed in claim 1, wherein the human membrane protein is of human, animal or recombinant origin.

12. A reactivated human membrane protein made by the process of claim 1.

* * * * *